US008592358B2

(12) United States Patent
Beilfuss et al.

(10) Patent No.: US 8,592,358 B2
(45) Date of Patent: *Nov. 26, 2013

(54) STORAGE-STABLE, SYNERGISTIC MICROBICIDAL CONCENTRATES CONTAINING AN ISOTHIAZOLONE, AN AMINE AND AN OXIDIZING AGENT

(75) Inventors: Wolfgang Beilfuss, Hamburg (DE); Ralf Gradtke, Tornesch (DE); Ingo Krull, Kummerfeld (DE); Jennifer Knopf, Hamburg (DE)

(73) Assignee: L'Air Liquide, Societe Anonyme pour l'Etude et l'Exploitation des Procedes Georges Claude, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/497,092

(22) PCT Filed: Sep. 22, 2010

(86) PCT No.: PCT/EP2010/063980
§ 371 (c)(1),
(2), (4) Date: Mar. 20, 2012

(87) PCT Pub. No.: WO2011/039088
PCT Pub. Date: Apr. 7, 2011

(65) Prior Publication Data
US 2012/0189603 A1 Jul. 26, 2012

(30) Foreign Application Priority Data
Oct. 2, 2009 (DE) .......................... 10 2009 048 189

(51) Int. Cl.
*C11D 3/48* (2006.01)
*C11D 1/58* (2006.01)

(52) U.S. Cl.
USPC ........... 510/382; 510/286; 510/287; 510/302; 510/308; 510/322; 510/327; 510/329; 510/332; 510/342; 510/373; 510/375; 510/432; 510/494

(58) Field of Classification Search
USPC ......... 510/286, 287, 302, 308, 322, 327, 329, 510/332, 342, 373, 375, 382, 432, 494; 514/372, 663, 665, 666, 667; 548/212, 548/213, 215, 222
See application file for complete search history.

(56) References Cited

U.S. PATENT DOCUMENTS

| 4,906,651 | A | 3/1990 | Hsu |
| 5,153,213 | A | 10/1992 | Schmidt |
| 5,276,047 | A | 1/1994 | Eggensperger et al. |
| 6,361,788 | B1 | 3/2002 | Antoni-Zimmermann et al. |
| 2003/0232906 | A1 | 12/2003 | Ghosh |
| 2004/0035803 | A1 | 2/2004 | Cronan et al. |
| 2008/0063723 | A1* | 3/2008 | Choi et al. ................... 424/489 |
| 2008/0280792 | A1 | 11/2008 | Williams |

FOREIGN PATENT DOCUMENTS

| DE | 40 33 272 | 10/1991 |
| DE | 195 34 532 | 3/1997 |
| EP | 0 436 744 | 7/1991 |
| EP | 0 544 418 | 6/1993 |
| EP | 0 773 282 | 5/1997 |
| EP | 0 777 966 | 6/1997 |
| EP | 1 185 401 | 3/2002 |
| EP | 1 005 271 | 11/2002 |
| JP | 2005 232070 | 9/2005 |
| WO | 20071032918 | 3/2007 |
| WO | 2008/018386 | 2/2008 |

OTHER PUBLICATIONS

Fewings et al., Contact Dermatitis 41:1-13 (1999).*
Kuzniak et al., Folia Microbiol. 51(1): 38-44 (2006).*
Baldry, J. Appl. Bacteriol. 54: 417-423 (1983).*
International Search Report dated Mar. 24, 2011, corresponding to PCT/EP2010/063980.
German Office Action dated Jan. 13, 2010, corresponding to Foreign Priority Application No. 10 2009 048 189.3.

* cited by examiner

Primary Examiner — Charles Boyer
(74) Attorney, Agent, or Firm — Young & Thompson

(57) ABSTRACT

A microbicidal composition in the form of a concentrate includes a) one or more isothiazolin-3-ones, b) one or more organic amines with an alkyl group having at least 8 carbon atoms and c) one or more oxidizing agents. The concentrate is storage-stable and is used for the preservation of technical and domestic products.

19 Claims, No Drawings

STORAGE-STABLE, SYNERGISTIC MICROBICIDAL CONCENTRATES CONTAINING AN ISOTHIAZOLONE, AN AMINE AND AN OXIDIZING AGENT

The present invention relates to a microbicidal composition in the form of a concentrate and to the use of the concentrate for the preservation of technical and domestic products.

The prior art discloses a large number of active ingredients for the preservation of technical and domestic products. Inter alia, isothiazolin-3-ones (hereinbelow isothiazolones) are used as preservation active ingredients. For example, EP 1 005 271 A1 discloses a mixture of 2-methylisothiazolone (methylisothiazolone, MIT) and 1,2-benzisothiazolone (BIT). This mixture is sold by Thor Chemie GmbH (Speyer, Federal Republic of Germany) as Acticide® MBS. In many cases, however, the effectiveness of Acticide® MBS is still not satisfactory, for example the activity spectrum is not sufficiently broad, the required use concentration is too high, or the product cannot be used for cost reasons.

In addition, DE 40 33 272 C1 discloses combinations of BIT and organic amines (such as bis(aminopropyl)dodecylamine=laurylpropylenediamine).

In investigations by the applicant, it has now been found that combinations of certain isothiazolones such as MIT with organic amines are extraordinarily unstable in aqueous solution.

The object of the present invention was therefore to provide a stable (in particular active-ingredient-stable), storable composition in the form of a concentrate with improved effectiveness and a broader spectrum of action, the components of which interact synergistically and permit a cost-effective use. The composition should also be stable and storable at a pH of from 8 to 10 and be able to be used economically for the use in domestic products and technical products.

This object is achieved through the provision of a microbicidal composition in the form of a concentrate which comprises
  a) one or more isothiazolones,
  b) one or more organic amines with an alkyl group having at least 8 carbon atoms and
  c) one or more oxidizing agents.

The invention is based inter alia on the fact that it has surprisingly been found that oxidizing agents are suitable for stabilizing combinations of isothiazolones with organic amines as concentrate, particularly if, as isothiazolone a), MIT or a mixture of the isothiazolones MIT and BIT are used together with the organic amine b).

a) Isothiazolone

Examples of isothiazolones according to the invention are: MIT, BIT, 2-n-octylisothiazolone (OIT), 5-chloro-2-methylisothiazolone (CMI), n-methylbenzisothiazolone (Me-BIT), n-butylbenzisothiazolone (n-Bu-BIT), 4,5-dichloro-2-octylisothiazolone (DCOIT) or mixtures thereof. It is also possible to use salts of isothiazolones, in particular salts of the specified isothiazolones. Preference is also given to halogen-free isothiazolones, such as MIT, BIT, OIT, Me-BIT, n-Bu-BIT or mixtures thereof. Preference is also given to the combination of halogen-free isothiazolones with sulphite salts such as disulphite or hydrogensulphite; this combination produces the so-called Bunte salts, as known to the person skilled in the art.

In one preferred embodiment, a mixture of at least two isothiazolones is used, particularly preferably at least two halogen-free (in particular chlorine-free) isothiazolones.

If the isothiazolone is present as salt (for example as Bunte salt), then the amount of component a) is stated relative to the isothiazolone as pure active ingredient without taking into consideration the salt formation. The concentration of component a) in the concentrate is preferably 0.5 to 15% by weight, more preferably 1 to 10% by weight, in particular 2 to 8% by weight, such as, for example, 5% by weight (stated as pure active ingredient).

As component a), particular preference is given to a mixture of BIT and MIT, and the presence of further isothiazolones is in this case preferably excluded. Here, the BIT/MIT weight ratio is typically 1:10 to 10:1, preferably 1:4 to 4:1, such as for example 1:1.

As component a), preference is also given to MIT, and the presence of further isothiazolones is in this case preferably excluded.

Moreover, as component a), preference is given to a mixture of OIT and BIT, and the presence of further isothiazolones is in this case preferably excluded. In this embodiment, the OIT/BIT weight ratio is typically 1:10 to 10:1, preferably 1:4 to 4:1, such as for example about 1:1.

Moreover, as component a), preference is also given to OIT, and the presence of further isothiazolones is in this case preferably excluded.

Furthermore, it is preferred that the use solution comprises no CMI. The use solution particularly preferably comprises no chlorine-containing isothiazolone.

In addition, a mixture of OIT and MIT is preferred as component a). Here, the OIT/MIT weight ratio is typically 1:10 to 10:1, preferably 1:4 to 4:1, such as for example about 1:1.

b) Organic Amine

The at least one organic amine used as component b) has an alkyl group with at least 8 carbon atoms. This alkyl group can be a terminal (i.e. alkyl) radical or bridge-position (i.e. alkylene) radical.

Examples of organic amines according to the invention with an alkyl group having at least 8 carbon atoms are the organic amines of the formula I specified in DE 40 33 272 C1.

$$R-N\begin{matrix}(CH_2)_n-NH_2 \\ \\ (CH_2)_m-NH_2\end{matrix} \qquad (I)$$

In this formula I, R is a straight-chain or branched-chain alkyl or alkylene radical having 8 to 22 carbon atoms, and n+m=2 to 12. Preferably, n+m=3 to 10, such as 4 to 8, in particular n=m=3. The organic amines according to the formula I are C6- to C22- and preferably C10- to C14-straight-chain or branched-chain alkylamines or alkylenamines, such as, for example, derivatives of fatty amines R—NH2, in which R is a coconut fatty alkyl radical (C8 to C18-, predominantly C12- to C14-alkyl), an oleyl radical (predominantly C18-alkenyl), a stearyl radical (C16-alkyl) or a tallow fatty alkyl radical (C16- to C18-alkyl or alkenyl).

It is also possible to use amine salts.

Besides the one alkyl group having at least 8 carbon atoms, the organic amine used according to the invention can also have one or more further alkyl groups. This one further alkyl group (these two or more alkyl groups) preferably have one to five carbon atoms, preferably two to four carbon atoms, such as three carbon atoms.

Preference is given to primary, secondary or tertiary alkylamines, alkyldiamines, alkyltriamines or alkylpolyamines having at least one (and preferably at least two, such as at least three) alkyl groups having at least 8 carbon atoms, preferably at least 12 carbon atoms, particularly preferably at least 15 carbon atoms, in particular at least 18 carbon atoms, such as at least 24 carbon atoms, or mixtures thereof.

Particular preference is given to N-dodecylpropane-1,3-diamine and bis(aminopropyl)dodecylamine (Lonzabac® 12). Particular preference is given to bis(aminopropyl)dodecylamine.

If the organic amine is present as salt, then the amount of component b) is stated relative to the organic amine without taking into consideration the salt formation. The concentration of component b) in the concentrate is preferably 0.5 to 15% by weight, more preferably 1 to 10% by weight, in particular 2 to 5% by weight, such as for example about 3% by weight.

c) Oxidizing Agents

Preferred oxidizing agents according to the invention are inorganic or organic oxidizing agents, such as chloric acid, perchloric acid, bromic acid, iodic acid, periodic acid or salts thereof, nitrates (alkali metal and alkaline earth metal nitrates, such as e.g. $NaNO_3$, $KNO_3$ and $Mg(NO_3)_2$), $H_2O_2$, $H_2O_2$ donors, such as sodium percarbonate, sodium perborate, urea peroxide, peroxides, such as t-butyl peroxide, percarboxylic acids, such as peracetic acid etc. or salts thereof, persulphuric acids and salts thereof (caroates), peroxodisulphonic acid or salts thereof, perphosphoric acids or salts thereof, and transition metals such as salts of Cu, Zn and Fe in relatively high oxidation states.

Examples of compounds which act as oxidizing agents within the context of the invention are also disulphides, such as pyrion disulphide, oxidases, such as glucose peroxidase, or mixtures of these oxidizing agents.

Preferred oxidizing agents are potassium iodate, sodium periodate, sodium bromate, H2O2, Cu(II) salts (in particular Cu(II) complexes soluble in a weakly alkaline medium at a pH of from 7 to 10).

Alternatively, preference is given to oxidizing agents with an independent biocidal effectiveness, such as oxidases, H2O2, peracetic acid, caroate and pyrion disulphide.

p

Particularly preferred oxidizing agents are potassium iodate, sodium bromate, H2O2 and Cu(II) complexes, where potassium iodate is very particularly preferred as oxidizing agent.

The concentration of component c) in the concentrate is preferably 0.01 to 10% by weight, more preferably 0.05 to 1% by weight, in particular 0.08 to 0.5% by weight, such as for example 0.1 to 0.3% by weight.

Further Constituents

The composition according to the invention optionally comprises d) solvents and/or e) further microbicidal active ingredients, functional additives or auxiliaries.

Suitable solvents are: water, alcohols, such as ethanol, propanols, benzyl alcohol, glycols, such as ethylene glycol, propylene glycols, such as dipropylene glycol, butanediols, glycol ethers, such as butyl glycol, butyl diglycol, phenoxyethanol, phenoxypropanols, polyols, such as glycerol, alkanediols and alkyl glycerol ethers, and mixtures thereof. Preference is given to using VOC (volatile organic compounds)-free or low-VOC solvents. The solvent is preferably water.

The concentration of component d) in the concentrate is preferably 40 to 98.99% by weight, more preferably 60 to 98% by weight, in particular 80 to 96% by weight, such as for example 88 to 90% by weight.

The concentrate preferably comprises d) water in an amount of from 40 to 98.99% by weight, more preferably 60 to 98% by weight, in particular 80 to 96% by weight, such as for example 88 to 90% by weight.

Other suitable biocidal active ingredients are biocides from the Biocidal Products Directive (BPD, 98/8/EC), preferably C5-C14-alkyl glycol ethers such as Sensiva® SC 50 (1-(2-ethylhexyl)glycerol ether) and C5-C12-alkanediols, such as octanediol-1,2, hexanediol-1,2, pentanediol-1,2 and decanediol-1,2, benzyl alcohol, phenoxyethanol, phenoxypropanols, phenethyl alcohol, phenylpropanols. Particular preference is given to Sensiva® SC 50 and octanediol-1,2, benzyl alcohol and phenoxyethanol. If the compositions according to the invention comprise further biocidal active ingredients, noteworthy further synergistic increases in effect sometimes arise.

Suitable functional additives are:
complexing agents (such as EDTA, NTA),
thickeners,
fillers,
antioxidants (such as vitamin E, BHA and BHT),
alkalizing agents, such as NaOH, KOH, alkali metal carbonate, alkali metal hydrogencarbonate, ammonia, low molecular weight amines or alkanolamines,
acidifying agents, such as carboxylic acids, such as acetic acid, preferably hydroxycarboxylic acids, such as lactic acid, citric acid,
buffers,
corrosion inhibitors (such as benzotriazole),
wetting agents and
low-temperature stabilizers.

The concentrates according to the invention are preferably clear and homogeneous and are in the form of liquids, preferably aqueous solutions. They are adequately colour-stable, low-temperature-stable, storage-stable and active-ingredient-stable.

Alternatively, the concentrates according to the invention are in the form of low-viscosity to medium-viscosity, flowable compositions.

In a further alternative embodiment, the concentrates according to the invention are in the form of semisolid, pasty compositions.

The pH of the concentrate is preferably in the range from 2 to 14, more preferably 4 to 12, in particular 6 to 11, even more preferably 8 to 10.

Preference is given to a liquid concentrate which comprises
a) at least two biocidally effective isothiazolones,
b) at least one biocidally effective organic amine,
c) at least one selected oxidizing agent,
d) at least one solvent (preferably water) and
e) optionally further microbicidal active ingredients, functional additives or auxiliaries.

In one particularly preferred embodiment, the composition is present as liquid concentrate in completely demineralized water with a content of
a) 1) BIT in an amount of from 0.5 to 10% by weight, preferably 1 to 7% by weight, in particular 2 to 6% by weight, and
2) MIT in an amount of from 0.5 to 10% by weight, preferably 1 to 7% by weight, in particular 2 to 6% by weight,
b) bis(aminopropyl)dodecylamine in an amount of from 0.5 to 10% by weight, preferably 1 to 7% by weight, in particular 2 to 6% by weight, and
c) potassium iodate in an amount of from 0.05 to 1% by weight, preferably 0.08 to 0.5% by weight, in particular 0.1 to 0.3% by weight.

In a further alternatively preferred embodiment, the composition is present as liquid concentrate in completely demineralized water with a content of a) 1) OIT in an amount of from 0.5 to 10% by weight, preferably 1 to 7% by weight, in particular 2 to 6% by weight, and
2) MIT in an amount of from 0.5 to 10% by weight, preferably 1 to 7% by weight, in particular 2 to 6% by weight,
b) bis(aminopropyl)dodecylamine in an amount of from 0.5 to 10% by weight, preferably 1 to 7% by weight, in particular 2 to 6% by weight, and
c) potassium iodate in an amount of from 0.05 to 1% by weight, preferably 0.08 to 0.5% by weight, in particular 0.1 to 0.3% by weight.

The invention also relates to the use of oxidizing agents according to the invention for the stabilization of (preferably halogen-free) isothiazolones such as MIT, OIT or derivatives thereof in the presence of biocidal organic amines, preferably in the alkaline range.

Moreover, the invention relates to the use of oxidizing agents according to the invention for the stabilization of BIT-containing preparations in the presence of halogen-free isothiazolones such as MIT, OIT or derivatives thereof, preferably in the presence of biocidal organic amines, preferably in the alkaline range.

The invention also relates to the preparation of the compositions according to the invention and to the use thereof as addition to substances which can be attacked by harmful microorganisms (e.g. as pot preservative).

For the preparation of MIT/BIT-containing preparations, water is introduced as initial charge, BIT is added and, to prepare a clear solution, an alkalizing agent, such as NaOH 45% strength, is added and the mixture is adjusted to a pH of 8.2 to 8.7, preferably 8.5 (in the event of too low a pH, BIT could precipitate out, and in the event of too high a pH the MIT subsequently added becomes unstable, pH adjustment e.g. with NaOH and/or acetic acid). Then, the other formulation constituents such as MIT are added, the mixture is further stirred for a short time and, if necessary, filtered. The compositions are preferably prepared at room temperature with stirring.

Consequently, the invention also relates to the use of a combination of components a), b) and c) of the composition according to the invention for the preservation of water-containing or water-dilutable technical or domestic products.

The synergistically effective components a), b) and c) may—preferably—be present in a product, e.g. a liquid concentrate, and be metered into the end product or intermediate product to be preserved in a known manner. The synergistically effective components a), b) and c) may, however, also be present in two or more separate products (solid and/or liquid) and be metered into the end product or intermediate product to be preserved in a known manner.

Moreover, the invention relates to a technical or domestic product which preferably comprises at least 0.001 percent by weight, more preferably at least 0.01 percent by weight, of the composition according to the invention present as concentrate (or the corresponding amounts of components a), b) and c) if these are added separately).

The product, e.g. the application solution, thus comprises for example
a) 25 to 300 ppm of isothiazolone, preferably 50 to 150 ppm of isothiazolone, where a mixture (preferably a 1:1 mixture based on the weight) of MIT and BIT is particularly preferred, and
b) 15 to 180 ppm of amine, preferably 30 to 90 ppm of amine.

Preferred products are low in anionic surfactant and preferably comprise less than 5 percent by weight of anionic surfactant. Examples of products are water-based products of all types, such as polymer dispersions, paints, plasters, adhesives, sealing compositions, paper coating compositions, textile softening and sizing compositions, washing raw materials, cleaning and domestic products, surfactants, polishing compositions, spinning baths, cooling lubricants, leather treatment compositions and silicone and bitumen emulsions.

The advantages of the present invention arise in particular from the following examples (unless stated otherwise, quantitative data are based on the weight):

EXAMPLES

The following substances were used:

| | |
|---|---|
| Lonzabac ® 12.100 (Grotan ® A12) | comprises ca. 91% bis(aminopropyl)dodecylamine, the remainder is aminopropyldodecylamine and dodecylamine, |
| Kordek ® 573 F | a 50% strength aqueous MIT solution, |
| Kathon ® 893 | OIT, 45% strength in propylene glycol, |
| Parmetol ® MBS | 2.5% MIT and 2.5% BIT. |

A) Comparative Examples

In preliminary experiments relating to the present invention, it was surprisingly found that a combination of 2.5% by weight of MIT, 2.5% by weight of BIT and 3.0% by weight of Lonzabac 12.100 is completely unstable in aqueous solution. For this, a composition was prepared from the following constituents:

| Constituents (composition 1A) | Percent by weight |
|---|---|
| Completely demineralized water | 84.84 |
| Benzisothiazolone, 82.8% strength (water-moist solid) | 3.02 |
| NaOH, 45% strength in water | 1.60 |
| Lonzabac 12.100 | 3.00 |
| Adjust to pH 8.5 with lactic acid | 2.54 |
| Kordek 573 F | 5.00 | and stored in 100 ml polyethylene bottles. The appearance and the content in the composition of MIT and BIT changed during storage at 25° C. and 40° C. as follows:

| | Start | 1 Month/25° C. | 1 Month/40° C. |
|---|---|---|---|
| Appearance | clear, yellow | turned orange* | turned dark* |
| MIT % | 2.05 | <0.01 | <0.01 |
| BIT % | 2.41 | 0.12% | <0.01 |

*Precipitate

Some of the MIT is already degraded within a few hours. After storage for 1 month at 25° C., the content of MIT has dropped below the detection limit and the content of BIT has dropped by more than 95%. In the case of storage for 1 month at 40° C., the content of the active ingredients MIT and BIT has dropped below the detection limit.

These results were also confirmed by the following investigations relating to the behaviour of MIT on its own. To prepare the comparison compositions 1B to 1F, the amine was introduced as initial charge in completely demineralized (dem.) water, the pH was adjusted using the stated acid, MIT was added and the mixture was topped up to 100% with completely demineralized water:

| Constituents | 1B | 1C | 1D | 1E | 1F |
|---|---|---|---|---|---|
| Dem. water | 60.0 | 60.0 | 60.0 | 60.0 | 60.0 |
| Lonzabac 12.100 | 3.0 | 3.0 | 3.0 | 3.0 | 3.0 |
| Acetic acid, 60% strength, to pH | 7.0 | 9.0 | 5.5 | 7.0 | 9.0 |
| Lactic acid, 85% strength, to pH | 2.5 | 2.5 | 2.5 | 2.5 | 2.5 |
| MIT | | | | | |
| Dem. water ad | 100 | 100 | 100 | 100 | 100 |
| Start | | | | | |
| Appearance | Clear, yellow solution | Clear, yellow solution | Clear, yellow solution | Clear, yellow solution | Clear, yellow solution |
| Content of MIT | 2.49% | <0.01% | 2.50% | 2.47% | <0.01% |
| After 1 month at 40° C. | | | | | |
| Appearance | Precipitate in dark-red solution, nasty odour | Precipitate in dark-red solution, nasty odour | Precipitate in dark-red solution, nasty odour | Precipitate in dark-red solution, nasty odour | Precipitate in dark-red solution, nasty odour |
| Content of MIT | <0.01% | <0.01% | <0.01% | <0.01% | <0.01% |

It is thus demonstrated that the instability of isothiazolones observed in the presence of amine arises not only with mixtures of isothiazolones (such as BIT/MIT), but also with specific individual isothiazolones such as MIT.

B) Examples According to the Invention

Compositions according to the invention were formulated from the following constituents (data in % by weight):

| Constituents | 2A | 2B |
|---|---|---|
| Completely demineralized water | 85.21 | 85.15 |
| Benzisothiazolone, 82.8% strength (water-moist solid) | 3.02 | 3.02 |
| NaOH, 45% strength in water | 1.60 | 1.60 |
| Lonzabac 12.100 | 3.00 | 3.00 |
| Sodium metaperiodate | 0.10 | — |
| Potassium iodate | — | 0.10 |
| Adjust to pH 8.5 with acetic acid (60% strength) | 2.07 | 2.13 |
| Kordek 573 F | 5.00 | 5.00 |

C) Synergistic Effect of Isothiazolone and Organic Amine

The excellent synergistic effect of the combination of isothiazolone (1, 2.5% by weight of MIT+2.5% by weight of BIT, Acticide MBS) and amine (2, Lonzabac 12.100, Grotan A12) is demonstrated by the following results of germ-count reduction tests. The pH was adjusted to 8.2 with HCl.

i) Germ-Count Reduction Test

| Aim | It is the aim of the germ-count reduction test to find a suitable use concentration and action time for an active ingredient under test. |
|---|---|
| Solutions and nutrient media | CSA (casein peptone-soybean flour peptone agar) CSL (casein peptone-soybean flour peptone solution) SA (Sabouraud agar) NaCl (physiological sodium chloride solution, 0.85%) |
| Test germs | *Aspergillus niger* ATCC 6275 |
| | *Candida albicans* ATCC 10231 |
| | *Pseudomonas aeruginosa* ATCC 15442 |
| | *Pseudomonas fluorescens* ATCC 17397 |
| | *Pseudomonas putida* ATCC 12633 |
| | *Staphylococcus aureus* ATCC 6538 |

| | 2A | | | | | 2B | | | | | |
|---|---|---|---|---|---|---|---|---|---|---|---|
| | | 1 Month | | 3 Months | | | 1 Month | | 3 Months | | |
| | Start | 25° C. | 40° C. | −5° C. | 25° C. | Start | 25° C. | 40° C. | −5° C. | 25° C. | 40° C. |
| Appearance | * Slightly opaque, yellow | Clear, yellow | Clear, rich yellow | Frozen | Clear yellowish | Very slightly opaque, yellow | Clear, yellow | Clear, rich yellow | Frozen | Clear, yellow | Clear, orange-yellow |
| H/G colour Number | 243/1.7 | 547/3.6 | ***/5.0 | — | 702/4.0 | 238/1.6 | 499/3.4 | 979/4.9 | — | 640/3.9 | ***/6.1 |
| Density | 1.0207 | 1.0210 | 1.0213 | — | 1.0208 | 1.0216 | 1.0219 | 1.0219 | — | 1.0217 | 1.0217 |
| Refraction | 1.3528 | 1.3528 | 1.3528 | — | 1.3528 | 1.3526 | 1.3528 | 1.3528 | — | 1.3529 | 1.3527 |
| MIT % | 2.45 | 2.50 | 2.43 | — | 2.51 | 2.45 | 2.49 | 2.49 | — | 2.47 | 2.40 |
| BIT % | 2.41 | 2.42 | 2.36 | — | 2.44 | 2.40 | 2.38 | 2.38 | — | 2.44 | 2.33 |

* Stir overnight. H/G colour number = Hazen or Gardner colour number.

Note:
The samples stored at −5° C. are homogeneous and clear after warming to room temperature.

Cultivation and Preparation of the Inoculation Solutions
Bacteria

24-Hour CSL cultures are prepared from 24-hour CS slant agar cultures of *Staphylococcus aureus/Pseudomonas aeruginosa*. Incubation takes place at 37° C.

48-Hour CSL cultures are prepared from 48-hour CS slant agar cultures of *Pseudomonas fluorescens/Pseudomonas putida*. Incubation takes place at 25° C.

The titre of the bacteria suspensions is ca. 109 CFU/ml.
Yeasts

A 4-day-old *Candida albicans* culture (CSA+grape sugar) is elutriated with 5 ml of physiological sodium chloride solution and adjusted in accordance with a barium sulphate standard (see DVG Guideline). The titre of the *Candida albicans* suspension is 108 CFU/ml.
Moulds A 7-14-day-old *Aspergillus niger* culture on Sabouraud agar is elutriated with 5 ml of NaCl, filtered through a glass filter containing glass wool and topped up to 200 ml. This suspension has a titre of ca. 107 CFU/ml.
Procedure A dilution series of four concentrations is prepared from the active ingredient to be tested and poured into 10 ml sterile tubes. One dilution series is required per test germ. Each tube is inoculated with 0.1 ml of the individual germ suspensions.

After 6, 24, 48 and 168 hours, the samples are streaked using sterile glass rods on CSA or Sabouraud agar. The bacteria are streaked on CSA and incubated for 48 hours at 37° C. (*Pseudomonas aeruginosa* and *Staphylococcus aureus*) or 25° C. (*Pseudomonas fluorescens/Pseudomonas putida*). The fungi are streaked on Sabouraud agar and incubated for 48 hours at 37° C. (*Candida albicans*) and 25° C. (*Aspergillus niger*).

Assessment
 −=growth-free
 +=slight growth
 ++=moderate growth
 +++=considerable growth
 ++++=massive growth
 L=lawn-like growth ii) Results

| Test material | 1 h | 3 h | 6 h | 24 h |
|---|---|---|---|---|
| *P. aeruginosa* | | | | |
| Sterile town water | L | L | L | L |
| +0.05% 1 | L | L | L | ++ |
| +0.1% 1 | L | L | L | + |
| +0.2% 1 | L | L | L | − |
| +0.3% 1 | L | L | L | − |
| +0.01% 2 | + | + | − | − |
| +0.05% 1 | − | − | − | − |
| +0.01 2 | | | | |
| +0.1% 1 | − | − | − | − |
| +0.01 2 | | | | |
| +0.2% 1 | − | − | − | − |
| +0.01 2 | | | | |
| +0.3% 1 | − | − | − | − |
| +0.01 2 | | | | |
| *P. funiculosum* | | | | |
| Sterile town water | L | L | L | L |
| +0.05% 1 | L | L | L | +++ |
| +0.1% 1 | L | L | L | +++ |
| +0.2% 1 | L | L | L | ++ |
| +0.3% 1 | L | L | L | + |
| +0.01% 2 | − | − | − | − |
| +0.05% 1 | − | − | − | − |
| +0.01 2 | | | | |
| +0.1% 1 | − | − | − | − |
| +0.01 2 | | | | |
| +0.2% 1 | − | − | − | − |
| +0.01 2 | | | | |
| +0.3% 1 | − | − | − | − |
| +0.01 2 | | | | |
| *S. aureus* | | | | |
| Sterile town water | L | L | L | L |
| +0.05% 1 | L | L | L | L |
| +0.1% 1 | L | L | L | L |
| +0.2% 1 | L | L | L | L |
| +0.3% 1 | L | L | L | +++ |
| +0.01% 2 | − | − | − | − |
| +0.05% 1 | − | − | − | − |
| +0.01 2 | | | | |
| +0.1% 1 | − | − | − | − |
| +0.01 2 | | | | |
| +0.2% 1 | − | − | − | − |
| +0.01 2 | | | | |
| +0.3% 1 | − | − | − | − |
| +0.01 2 | | | | |
| *A. niger* | | | | |
| Sterile town water | L | L | L | L |
| +0.05% 1 | L | L | L | L |
| +0.1% 1 | L | L | L | L |
| +0.2% 1 | L | L | L | L |
| +0.3% 1 | L | L | L | L |
| +0.01% 2 | − | − | − | − |
| +0.05% 1 | − | − | − | − |
| +0.01 2 | | | | |
| +0.1% 1 | − | − | − | − |
| +0.01 2 | | | | |
| +0.2% 1 | − | − | − | − |
| +0.01 2 | | | | |
| +0.3% 1 | − | − | − | − |
| +0.01 2 | | | | |
| *E. coli* | | | | |
| Sterile town water | L | L | L | L |
| +0.05% 1 | L | L | L | +++ |
| +0.1% 1 | L | L | L | + |
| +0.2% 1 | L | L | L | − |
| +0.3% 1 | L | L | L | − |
| +0.01% 2 | + | − | − | − |
| +0.05% 1 | − | − | − | − |
| +0.01 2 | | | | |
| +0.1% 1 | − | − | − | − |
| +0.01 2 | | | | |
| +0.2% 1 | − | − | − | − |
| +0.01 2 | | | | |
| +0.3% 1 | − | − | − | − |
| +0.01 2 | | | | |
| *C. albicans* | | | | |
| Sterile town water | L | L | L | L |
| +0.05% 1 | +++ | +++ | +++ | +++ |
| +0.1% 1 | +++ | +++ | +++ | +++ |
| +0.2% 1 | +++ | +++ | +++ | +++ |
| +0.3% 1 | +++ | +++ | +++ | +++ |
| +0.01% 2 | − | − | − | − |
| +0.05% 1 | − | − | − | − |
| +0.01 2 | | | | |
| +0.1% 1 | − | − | − | − |
| +0.01 2 | | | | |
| +0.2% 1 | − | − | − | − |
| +0.01 2 | | | | |
| +0.3% 1 | − | − | − | − |
| +0.01 2 | | | | |

It is thus demonstrated that isothiazolone (a) and amine (b) have a synergistic effect. In particular the effectiveness against *P. aeruginosa* and *E. coli* should be emphasized. Only through the stabilization according to the invention of concentrates is it possible to utilize this synergy with a broad palette of isothiazolones and organic amines.

The invention claimed is:

1. A microbicidal composition in the form of a concentrate comprising:
   a) one or more isothiazolin-3-one (isothiazolone);
   b) one or more organic amine selected from N-dodecylpropane-1,3-diamine and bis(aminopropyl)-dodecylamine; and
   c) one or more oxidizing agent selected from the group consisting of: chloric acid, perchloric acid, bromic acid, iodic acid, periodic acid and salts thereof, nitrates, $H_2O_2$, $H_2O_2$— donors, sodium percarbonate, sodium perborate, urea peroxide, peroxides, t-butyl peroxide, percarboxylic acids, peracetic acid and salts thereof, persulphuric acids and salts thereof, peroxodisulphonic acid and salts thereof, perphosphoric acids and salts thereof, transition metals, Cu, Zn and Fe in relatively high oxidation states, disulphides, pyrion disulphide, oxidases, glucose peroxidase, potassium iodate, sodium periodate, sodium bromate, and Cu(II) salts.

2. The composition according to claim 1, wherein the one or more isothiazolone is selected from the group consisting of 2-methylisothiazolone (MIT), 1,2-benzisothiazolone (BIT), 2-n-octylisothiazolone (OIT), 5-chloro-2-methylisothiazolone, N-methylbenzisothiazolone, n-butylbenzisothiazolone, 4,5-dichloro-2-octylisothiazolone and mixtures thereof.

3. The composition according to claim 1, wherein the one or more isothiazolone comprises a mixture of MIT and BIT.

4. The composition according to claim 1, wherein the one or more isothiazolone comprises a mixture of MIT and OIT.

5. The composition according to claim 1, wherein the amount of component a) is 0.5 to 15% by weight.

6. The composition according to claim 1, wherein the amount of component b) is 0.5 to 15% by weight.

7. The composition according to claim 1, wherein the amount of component c) is 0.01 to 10% by weight.

8. The composition according to claim 1, further comprising
   additional microbicidal active ingredients, functional additives and/or auxiliaries.

9. The composition according to claim 1, wherein the composition has a pH in a range of from 2 to 14.

10. A method of preserving a water-containing or water-dilutable technical or domestic product, comprising metering into the product an effective amount of the composition according to claim 1.

11. The method according to claim 10, wherein the technical or domestic product is selected from the group consisting of polymer dispersions, paints, adhesives, paper coating compositions, textile softening and sizing compositions, washing raw materials, cleaning and polishing compositions, spinning baths, cooling lubricants, leather treatment compositions, silicone emulsions and bitumen emulsions.

12. A technical or domestic product comprising 0.01 to 1% by weight of the composition according to claim 1.

13. The composition according to claim 1, wherein the composition has a pH in the range of from 8 to 10.

14. A technical or domestic product comprising 0.1 to 0.3% by weight of the composition according to claim 1.

15. The method according to claim 10, wherein the composition is metered into the product to a final concentration of 0.01 to 1% by weight.

16. The composition according to claim 1, wherein the one or more organic amine comprises bis (aminopropyl)-dodecylamine.

17. The composition according to claim 1, wherein the one or more oxidizing agent comprises potassium iodate.

18. The composition according to claim 1, comprising 80-96% by weight of solvent selected from the group consisting of water, alcohols, ethanol, propanol, benzyl alcohol, glycols, ethylene glycol, propylene glycol, dipropylene glycol, butanediols, glycol ethers, butyl glycol, butyl diglycol, phenoxyethanol, phenoxypropanols, polyols, glycerol, alkanediols, alkyl glycerol ethers, and mixtures thereof.

19. The composition according to claim 1, comprising 80-96% by weight of water.

* * * * *